United States Patent [19]

Parker et al.

[11] Patent Number: 5,155,148

[45] Date of Patent: Oct. 13, 1992

[54] ESTER DERIVATIVES FROM P-HYDROXYDIPHENYLAMINE

[75] Inventors: Dane K. Parker, Massillon; Budd H. Sturm, Hartville, both of Ohio

[73] Assignee: The Goodyear Tire & Rubber Company, Akron, Ohio

[21] Appl. No.: 691,756

[22] Filed: Apr. 26, 1991

Related U.S. Application Data

[63] Continuation-in-part of Ser. No. 411,971, Sep. 25, 1989.

[51] Int. Cl.$^5$ .................. C08K 5/3417; C08K 5/3437; C07D 279/18
[52] U.S. Cl. ........................ 524/83; 524/89; 544/35
[58] Field of Search ............ 252/402; 524/83, 89, 524/240; 544/35

[56] References Cited

U.S. PATENT DOCUMENTS

| | | | |
|---|---|---|---|
| 3,240,703 | 3/1966 | Symon et al. | 252/45.7 |
| 4,077,942 | 3/1978 | Kline | 524/239 |
| 4,124,565 | 11/1978 | Kuezkowski | 524/239 |
| 4,141,848 | 2/1979 | Braid | 252/51.5 A |
| 4,853,446 | 8/1989 | De Wald et al. | 544/35 |
| 4,855,346 | 8/1989 | Batey et al. | 524/240 |
| 4,855,424 | 8/1989 | Hong et al. | 544/35 |
| 4,857,645 | 8/1989 | Adachi et al. | 544/35 |
| 4,877,824 | 10/1989 | Evans | 524/89 |

FOREIGN PATENT DOCUMENTS 0979531 12/1982 U.S.S.R. .................. 524/89

OTHER PUBLICATIONS

Thermochimica Acta, vol. 97, 1986, pp. 351–355, Amsterdam, NL; Y. I. Matusevich et al.: "Thermal Analysis of Stabilized Polymers", p. 352, line 3.

*Primary Examiner*—Kriellion S. Morgan
*Attorney, Agent, or Firm*—Bruce J. Hendricks

[57] ABSTRACT

The present invention relates to polymerizable esters containing derivatives from p-hydroxydiphenylamine which are useful in the stabilization of oxidizable organic materials such as rubber, oils and the like.

6 Claims, No Drawings

ESTER DERIVATIVES FROM P-HYDROXYDIPHENYLAMINE

This is a continuation-in-part of United States Ser. No. 07/411,971, filed Sept. 25, 1989.

BACKGROUND

Organic materials and especially polymers have proven to be difficult organic materials to stabilize against the deleterious affects of oxygen and ozone, particularly the unsaturated polymers, both natural and synthetic. Although many materials have been suggested and used as stabilizers in oxidizable organic materials, no completely satisfactory material has been found that will fully protect these materials under the widely different conditions to which they are subjected.

SUMMARY OF THE INVENTION

The present invention relates to a compound comprising an ester having the formula:

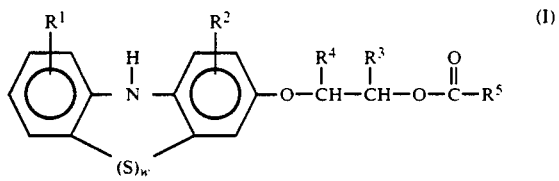

wherein $R^1$ and $R^2$ may be the same or different and are selected from the group of radicals consisting of hydrogen, alkyls having 1 to 18 carbon atoms, aryls having 6 to 18 carbon atoms, alkaryls having 7 to 18 carbon atoms and aralkyls having 7 to 18 carbon atoms; $R^3$ and $R^4$ may be the same or different and are selected from the group of radicals consisting of hydrogen and methyl; $R^5$ is a radical selected from the group consisting of alkenyls having 2 to 18 carbon atoms, and w is 0 or 1.

DETAILED DESCRIPTION

The present invention relates to chemical compositions which are useful in the stabilization of various organic materials. Representative of the organic materials that can benefit through the use of the compositions of the present invention include those materials that are susceptible to the oxidative degradation. Such materials include oils, fats, rubbers, plastics and the like. More specifically, this invention relates to the stabilization of polymeric materials that are subject to oxidative degradation. The polymers or rubbers that may be protected according to the present invention are vulcanized and unvulcanized polymers such as natural rubber and synthetic polymers. Examples of synthetic polymers containing carbon to carbon double bonds include rubbery diene polymers. Representative examples of the synthetic polymers that will benefit through the use of this invention are polychloroprene and homopolymers of conjugated 1,3-dienes such as isoprene and butadiene. Copolymers of conjugated 1,3-dienes such as isoprene and butadiene with up to 50 percent by weight of at least one copolymerizable monomer including ethylenically unsaturated monomers such as styrene and acrylonitrile are included. Butyl rubbers and polyurethanes which contain carbon to carbon double bonds can also benefit from the instant invention. The preferred synthetic polymers for use with the present invention are polybutadiene, polyisobutylene, EPDM, butadiene-styrene copolymers, polyisoprene, polychloroprene or mixtures thereof. In general, any organic material that may be subject to oxidative degradation will benefit from the incorporation of the composition of the present invention.

The ester containing composition of the present invention may be used with or without conventional additives such as stabilizers, vulcanizing agents, synergists, accelerators or other compounding ingredients. These additional additives may be used in conventional amounts known to those skilled in the art.

In order to effectively stabilize the organic material, varying proportions of the compound of the present invention may be added in a fashion customary to the industry. The amount of the composition of the present invention that is added may vary somewhat depending on the type and requirements of the material to be protected and the conditions to which the material will be subjected. For example, when the composition of the present invention is used in natural rubber or a synthetic polymer, the composition is generally used in an amount ranging from about 0.1 to about 10 parts per 100 parts of rubber (phr) or polymer. Preferably, the composition is added in amounts ranging from about 0.5 to about 5 phr.

The method of addition of the ester containing composition to the organic material to be stabilized is not critical. It may be added by any of the conventional means such as by adding to a polymer latex, milling on an open mill or by internal mixing. When the composition of the present invention is used to stabilize rubbers such as styrene/butadiene rubber or polybutadiene, a convenient method of incorporation consists of adding the composition to the polymer while it is in latex or cement forms. This is preferably done after the polymerization of the monomers is essentially complete.

As mentioned above, the composition of the present invention include those of the formula:

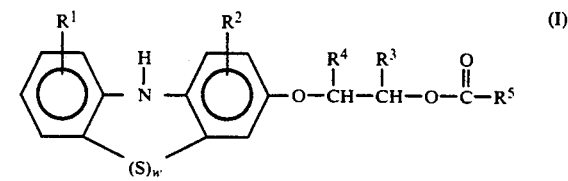

wherein $R^1$, $R^2$, $R^3$, $R^4$, $R^5$, and w are as described above. Preferably $R^1$ and $R^2$ are the same or different and are selected from the group of radicals consisting of hydrogen and methyl. $R^3$ and $R^4$ are each preferably hydrogen. $R^5$ is preferably selected from the group of radicals consisting of alkenyls having 2 to 4 carbon atoms, alkylidenes having 2 to 4 carbon atoms.

One of the advantages of the present invention is that depending on whether the composition of the present invention contains selected sites of unsaturation, wherein $R^5$ is an alkenyl having 2 to about 18 carbon atoms, the ester compounds may be copolymerized to impart oxidation and extraction resistance to the polymer composition. According to this embodiment, $R^5$ is preferably an alkenyl having 2 to 4 carbon atoms.

The compositions of the present invention are derivatives of substituted or unsubstituted p-hydroxydiphenylamine. To prepare the compositions of formula I, the substituted or unsubstituted hydroxydiphenylamine is first reacted with a carbonate of the formula:

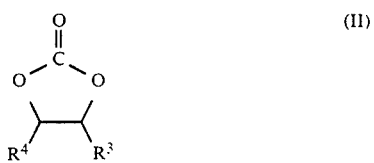 (II)

in the presence of a catalyst to form a hydroxyether of the formula:

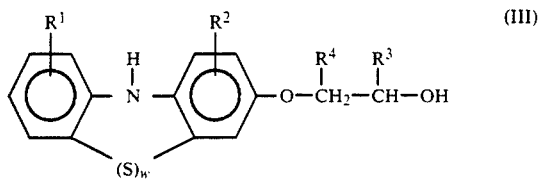 (III)

Representative of carbonates of formula II that may be used in the present invention are ethylene carbonate and propylene carbonate. Stoichiometrically, equimolar amounts of the carbonate of formula III and the substituted or unsubstituted p-hydroxydiphenylamine are needed to form the hydroxyether derivative of formula III; however, an excess of carbonate may be used. For example, the mole ratio of the substituted or unsubstituted p-hydroxydiphenylamine to carbonate may range from about 1:1 to 1:5. Preferably, the mole ratio of substituted or unsubstituted p-hydroxydiphenylamine to carbonate ranges from about 1:1 to 1:1.05. In order to maintain the respective mole ratio of the reactants, the total amount of each reactant may be initially charged or gradually added under suitable conditions to the reaction mixture.

While the conditions for the reaction between the substituted or unsubstituted p-hydroxydiphenylamine and carbonate may vary, the conditions should promote the formation of the hydroxyether of formula III. The reaction may be conducted at a temperature in the range of from about 100° to 250° C. Preferably the reaction is conducted at a temperature ranging from about 120° C. to about 220° C. A reaction temperature ranging from about 130° C. to about 200° C. is particularly preferred. The reaction pressure may range from atmospheric to subatmospheric. The reaction time will obviously vary depending on such factors as the reaction temperature, reaction pressure, purity of the reactants, reactivity of the catalyst, desired extent of reaction of reactants and amount of catalyst, to name a few. Generally, the reaction may be conducted over a period of from about two to about twenty hours.

The reaction vessel should be equipped with a means of agitation and gas outlet tube for the evolution of carbon dioxide.

The reaction between the substituted or unsubstituted p-hydroxydiphenylamine and the carbonate is conducted in the presence of a catalyst. The catalyst is generally dissolved or suspended in the reaction mixture. Examples of catalysts that may be used include lithium hydroxide, potassium hydroxide, quaternary ammonium or phosphonium salts. The catalyst is present in an amount sufficient to catalyze the reaction of the substituted or unsubstituted p-hydroxydiphenylamine and the carbonate. The amount of catalyst will vary depending on the particular catalyst selected.

When the catalyst is tetrabutylammonium bromide, it may be used in an amount of from about 0.5 to about 10.0% and preferably from 2.0 to about 5.0% based on the weight of the hydroxyether of formula III. When lithium hydroxide is the catalyst, 0.1% to 5.0% may be used, based on the weight of the hydroxyether of formula III, with a range of from about 0.5% to 2.0% being preferred.

The hydroxyether of formula III is reacted under transesterification conditions with an ester of the formula:

 (IV)

to form a composition of formula I. $R^6$ is generally a radical selected from the group consisting of alkyls having from 1 to 4 carbon atoms. Specific examples of esters that can be used include the alkyl esters of acrylic acid or methacrylic acid such as methyl methacrylate.

The mole ratio of the hydroxyether of formula III to the ester of formula IV may vary. Generally, there is a molar equivalent to a molar excess of the ester of formula IV. For example, the mole ratio of the hydroxyether of formula III to the ester of formula IV may be from about 1:1 to about 1:100. A mole ratio of the hydroxyether to the ester of from about 1:1.05 to about 1:15 is preferred.

In order to maintain the respective mole ratio of the reactants, the total amount of each reactant may be initially charged to the reactor or added gradually to the reaction mixture containing the reaction mixture.

While the conditions for the reaction between the hydroxyether of formula III and the ester of formula IV may vary, they should promote the transesterification reaction. The reaction between the hydroxyether of formula III and the ester of formula IV may be conducted at a temperature sufficient high to distill off by-product alcohol. Generally speaking the reactor temperature is in the range of from about 60° C. to 190° C. at atmospheric pressure. Preferably the reaction is conducted at a temperature ranging from about 60° C. to about 170° C. A reaction temperature ranging from about 65° C. to 140° C. is particularly preferred. The reaction pressure may range from atmospheric to subatmospheric. The reaction time will obviously vary depending on such factors as the reaction temperature, reaction pressure, purity of the reactants, reactivity of the catalyst, desired extent of reaction of reactants and amount of catalyst, to name a few. Generally, the reaction may be conducted over a period of from about 0.5 to about 20 hours.

The reaction vessel for the transesterification should be equipped with a means of agitation, an inlet for the introduction of an inert gas such as nitrogen, a means of removing the alcohol produced in the reaction. The alcohol may be removed by a distillation column with an appropriate reflux ratio.

The transesterification reaction is conducted in the presence of a catalyst. The catalyst is generally dissolved or suspended in the ester of formula IV. The catalyst may be one of a number of conventional catalysts including titanium, aluminum or tin alkoxides, potassium cyanide, p-toluenesulfonic acid, 3A, 4A or 5A molecular sieves and alkali metal alkoxides. The catalyst is present in an amount sufficient to catalyze the transesterification reaction. The amount of catalyst will vary depending on the particular catalyst selected. Since $R^5$ of formula IV contains unsaturation, a polymerization inhibitor is recommended. Examples of conventional polymerization inhibitors that may be used include fulvene compounds, quinone derivatives, nitrones, nitroso compounds, alkylated phenos, alkylated hydroxylamines, p-phenylenediamines, phenothiazine, t-butylcatecho, copper dithiocarbamate salt, 2,2,6,6-tetramethyl-4-hydroxypiperidine-4-oxyl and sodium anthraquinone sulfonate. The polymerization inhibitor should be present in an amount sufficient to inhibit the polymerization of the ester of formula IV. The inhibitor is typically present in an amount ranging from about 10 ppm to 1500 ppm, and preferably from 20 ppm to 600 ppm based on the weight of the ester of formula IV. The compositions of formula I when w is 1 may be prepared by first reacting a substituted or unsubstituted p-hydroxydiphenylamine with elemental sulfur in the presence of a catalyst. The reaction product of the reaction is a hydroxyphenothiazine of the formula:

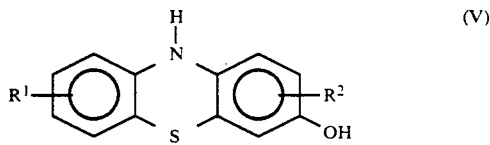

wherein $R^1$ and $R^2$ are as described above. The mole ratio of the p-hydroxydiphenylamine and the elemental sulfur is generally such that a molar excess of sulfur is present. The range may be from about 1:1 to about 1:3 with a range of from about 2:1 being preferred.

While the reaction conditions may vary, they should be such to promote the reaction between the sulfur and the hydroxydiphenylamine.reaction. The reaction may be conducted at a temperature in the range of from about 150° C. to 210° C. Preferably the reaction is conducted at a temperature ranging from about 180° C. to about 195° C. The reaction pressure may range from atmospheric to subatmospheric. The reaction time will obviously vary depending on such factors as the reaction temperature, reaction pressure, purity of the reactants, and the desired extent of reaction of reactants, to name a few. Generally, the reaction may be conducted over a period of from about 30 minutes to about 1 hour.

The reaction vessel should be equipped with a means of agitation and an inlet for the introduction of an inert gas such as nitrogen.

The reaction between the hydroxydiphenylamine and elemental sulfur is conducted in the presence of a catalyst. Examples of catalysts that may be used include iodine, $AlCl_3$ and/or the use of a $CO_2$ atmosphere during the reaction. The catalyst is present in an amount sufficient to catalyze the reaction between the elemental sulfur and the hydroxydiphenylamine. The amount of catalyst will vary depending on the particular catalyst selected. For example, when the catalyst is iodine, an amount of about 1 percent by weight based on the weight of hydroxydiphenylamine may be used.

The hydroxyphenothiazine of formula V is reacted with the cyclic carbonate of formula II under the conditions described above regarding the reaction between the carbonate and the p-hydroxydiphenylamine. Subsequently, the reaction product from the reaction of the carbonate and hydroxydiphenylamine is transesterified with an ester of formula IV to form the compound of formula I. The same conditions for the transesterification described above may be used.

The following examples are presented for the purposes of illustrating but not limiting the scope of the present invention.

EXAMPLE 1

Preparation of 4-(2-ethoxyethyl) diphenylamine methacrylate 17 6 grams (0.10 moles) of p-hydroxydiphenylamine, 0.6 grams (0.2 moles) ethylene carbonate and 1.0 gram (0.0031 moles) of tetrabutylammonium bromide were charged into a 100 ml, 3 neck, round bottom flask equipped with a magnetic stir bar, pot thermometer and a gas outlet tube attached to a bubbler. The mixture was heated to 160°-170° C. until the evolution of $CO_2$ ceased. At this point, gas chromatograph and thin layer chromatography analysis indicated no starting material was left in the reactor. The molten mass was cooled slightly and then poured into excess cold stirred water. The product crystallized rapidly, was filtered off and dried in air. The crude yield of 4-(2-hydroxyethoxy)diphenylamine was 22.0 grams and had a crude melting point of 69°-73° C. The crude product was recrystallized from toluene/hexane (10:1) to give a pink solid having a melting point of 79°-81° C.

88.0 grams (0.40 moles) of 4-(2-hydroxyethoxy) diphenylamine (prepared as above), 2.0 grams (0.008 moles) dibutyltin oxide, 400 grams (4.0 moles) methyl methacrylate and 0.02 grams of 4-hydroxy-2, 2,6,6-tetramethylpiperidine-N-oxyl (polymerization inhibitor) were charged to a 1 liter, 3 neck, round bottom flask equipped with a mechanical teflon paddle stirrer, pot thermometer, nitrogen inlet, septum sampling port and a 1-foot silvered vacuum pocketed column packed with stainless steel protrusion packing topped with a solenoid activated distillation splitter. The system was brought to reflux under a slow nitrogen purge. The azeotrope was distilled off. After 3 hours, thin layer chromatography analysis (85/15 $CHCl_3$ MeOH) indicated complete conversion to ester. The reaction was run one additional hour. The warm solution was then filtered through a bed of Filtrol 22 deodorizing clay. The clay cake was washed with toluene and the straw-colored filtrates then stripped at reduced pressure. The crude yield of product was 114.9 grams. The product slowly crystallized on standing several days. The melting point was 49°-51° C. Infrared spectra indicated the desired compound with $-NH$ str. at 3400 $cm^{-1}$, ester carbonyl at 1720 $cm^{-1}$, and $C-O$ str. at 1170 and 1230 $cm^{-1}$.

EXAMPLE 2

Preparation of 3-(2-ethoxyethyl) phenothiazine methacrylate 20.6 grams (0.10 moles) of 3-hydroxyphenothiazine, 11.44 grams (0.23 moles) of ethylene carbonate and 0.34 grams (0.001 moles) of tetrabutylammonium bromide were charged into a 100 ml, 3 neck, round bottom flask equipped with a magnetic stir bar, pot thermometer and a gas outlet tube attached to a bubbler. The mixture was heated at approximately 170° C. until the evolution of $CO_2$ ceased. At this point, thin layer chromataography analysis (85/15 $CHCl_3$/MeOH) indicated all the starting material had been converted after about 2.5 hours.

Approximately 25.0 grams (approximately 0.10 moles) of 3-(2-hydroxyethyl) phenothiazine (prepared as above) was dissolved in 105 grams (1.05 moles) of methyl methacrylate. The solution was charged to a 1 liter, 3 neck, round bottom flask equipped with a mechanical teflon paddle stirrer, nitrogen inlet and distillation heat, 0.5 grams (0.002 moles) of dibutyltin oxide and 0.02 grams of 4-hydroxy-2,2,6,6-tetramethylpiperidine-N-oxyl. A pot thermometer was attached to the flask and the mixture was heated with agitation. The azeotrope was distilled off (65°–85° C.). After 5 hours, thin layer chromatography (85/15 CHCl$_3$/MeOH) indicated complete conversion. After cooling the mixture slightly, 50 grams of Filtrol 22 decolorizing clay was added. The mixture was then diluted with 150 ml of toluene and filtered. After stripping off solvent at a reduced pressure, 32.8 grams of brown-amber semisolid was isolated.

EXAMPLE 3

Preparation of 4-(2-propoxypropyl) diphenylamine methacrylate 176 grams (1.0 mole) of p-hydroxydiphenylamine, 143 grams (1.40 moles) propylene carbonate and 3.15 grams (0.015 moles) of tetraethylammonium bromide were charged to a 500 ml 3-neck flask. A mechanical teflon paddle stirrer, condenser, gas outlet to bubbler and pot thermometer were attached to the flask. The mixture was stirred and heated to 175°–180° C. for 22 hours. Thin layer chromatography analysis of the mixture (85/15:CHCl$_3$/MeOH) showed that most of the starting material had been converted to 4-(2-hydroxypropyl) diphenylamine. The crude product amounted to approximately 278 grams of viscous oil.

278 grams of the 4-(2-hydroxypropyl) diphenylamine (approximately 1 mole), 400 grams (4.0 moles) of methyl methacrylate, 5.0 grams (0.02 moles) of dibutyltin oxide and 0.02 grams of 4-hydroxy-2,2,6,6-tetramethyl piperidine-N-oxyl were charged to a 1 liter 3 neck flask. To the flask was attached a pot thermometer, short distillation head and nitrogen inlet to the flask. The azeotrope was distilled off under slow nitrogen bleed. After 150 ml of azeotrope had distilled off (approximately 10 hours), an additional 250 ml of fresh methyl methacrylate was charged to the reaction flask and the distillation continued for another 4 more hours. Thin layer chromatography analysis (85/15:CHCl$_3$/MeOH) of the final product indicated almost complete conversion to 4-(2-propoxypropyl) diphenylamine methacrylate.

EXAMPLE 4

Several samples of antioxidants of the present invention were emulsion copolymerized at various levels in hot recipes with either butadiene or butadiene and styrene. The recipe for each copolymer is listed in Table I below along with the indication of whether the antioxidant of the present invention was prepared in accordance with Example 1, 2 or 3. The polymerizations were conducted at 60° C. for 24 hours. The copolymers were alcohol coagulated and the rubber was continuously extracted for 18 hours with hot methanol to remove any residual unreacted monomers. Samples of the dried extracted polymers were submitted for percent nitrogen analysis to determine the bound antioxidant content. Table I also lists the percent nitrogen of the extracted polymer as well as the parts of bound antioxidant (AO) in each polymer.

TABLE I

|   |   | Sample |   |   |   |   |   |   |   |   |   |   |   |
|---|---|---|---|---|---|---|---|---|---|---|---|---|---|
|   |   | 6 | 7 | 8 | 9 | 10 | 11 | 12 | 13 | 14 | 15 | 16 | 17 |
| (A) | Water | 220 | 220 | 220 | 220 | 220 | 220 | 220 | 220 | 220 | 220 | 220 | 220 |
|   | T.S.P.[1] | 0.5 | 0.5 | 0.5 | 0.5 | 0.5 | 0.5 | 0.5 | 0.5 | 0.5 | 0.5 | 0.5 | 0.5 |
|   | SDBS[2] | 20 | 10 | 5 | 2.5 | 2.5 | 2.5 | 20 | 10 | 5 | 2.5 | 2.5 | 2.5 |
| (B) | MIBK[3] | 80 | — | — | — | — | — | 80 | — | — | — | — | — |
|   | Example 1 | 40 | 40 | 20 | 10 | 10 | 5 | — | — | — | — | — | — |
|   | Example 2 | — | — | — | — | — | — | — | — | — | — | 10 | 5 |
|   | Example 3 | — | — | — | — | — | — | 40 | 40 | 20 | 10 | — | — |
|   | Styrene | — | — | 10 | 20 | — | 25 | — | — | 10 | 20 | — | 25 |
|   | AIBN[4] | 0.8 | 0.8 | 0.8 | 0.8 | 0.8 | 0.8 | 0.8 | 0.8 | 0.8 | 0.8 | 0.8 | 0.8 |
|   | t-dodecyl mercaptan | 0.6 | 0.6 | 0.6 | 0.6 | 0.6 | 0.6 | 0.6 | 0.6 | 0.6 | 0.6 | 0.6 | 0.6 |
| (C) | Butadiene | 60 | 60 | 70 | 70 | 90 | 70 | 60 | 60 | 70 | 70 | 90 | 70 |
|   | % N (extracted polymer) | 1.67 | 1.61 | 0.73 | 0.36 | 0.42 | 0.19 | 1.33 | 1.17 | 0.56 | 0.24 | 0.24 | 0.10 |
|   | Parts bound AO | 34.4 | 33.1 | 15.0 | 7.4 | 8.6 | 3.9 | 32.9 | 28.9 | 13.8 | 5.9 | 6.1 | 2.5 |

[1]Trisodium phosphate
[2]25% sodium dodecylbenzene sulfonate
[3]Methyl isobutyl ketone
[4]Azobis-(isobutyronitrile)

Various samples of the dried extracted rubber were analyzed by DSC to determine intrinsic oxidative stability (onset temperature of exothermic autocatalytic oxidation). Table II below lists the data from the DSC analysis along side the antioxidant (A.O.).

TABLE II

| Sample | A.O. | Onset Temp. (°C.) | Max. Temp. (°C.) |
|---|---|---|---|
| 9 | Ex. 1 | 228 | 237 |
| 10 | Ex. 1 | 228 | 237 |
| 11 | Ex. 1 | 221 | 228 |
| 12 | Ex. 3 | 209 | 246 |
| 13 | Ex. 3 | 222 | 247 |
| 14 | Ex. 3 | 228 | 242 |
| 15 | Ex. 3 | 226 | 230 |
| 16 | Ex. 2 | 223 | 226 |
| 17 | Ex. 2 | 218 | 222 |
| Control | No A.O. | 125 | 140 |

What is claimed is:

1. A compound comprising an ester having the structural formula:

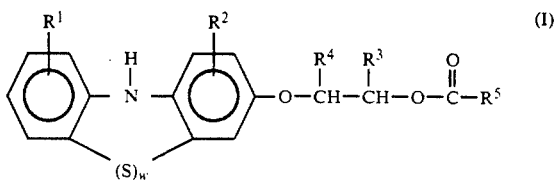

wherein $R^1$ and $R^2$ may be the same or different and are selected from the group of radicals consisting of hydrogen, alkyls having 1 to 18 carbon atoms, aryls having 6 to 18 carbon atoms, alkaryls having 7 to 18 carbon atoms and aralkyls having 7 to 18 carbon atoms: $R^3$ and $R^4$ may be the same or different and are selected from the group of radicals consisting of hydrogen and methyl: $R^5$ is a radical selected from the group consisting of alkenyls having 2 to 18 carbon atoms, and w is 0 or 1.

2. The compound of claim 1 wherein $R^5$ is an alkenyl having 2 to 4 carbon atoms.

3. The compound of claim 2 wherein R, $R^2$, $R^3$ and $R^4$ are each hydrogen, w is 0 and $R^5$ is an alkenyl having 3 carbon atoms.

4. The compound of claim 2 wherein R, $R^2$, $R^3$ $R^4$ are each hydrogen, w is 1 and $R^5$ is an alkenyl having 3 carbon atoms.

5. The compound of claim 2 wherein R, $R^2$, and $R^4$ are each hydrogen, w is $R^3$ is an alkyl having 1 carbon atoms, w is 0 and $R^5$ is an alkenyl having 3 carbon atoms.

6. A compound comprising the ester of claim 1 wherein said ester is compounded with an organic material selected from the group consisting of natural rubber, synthetic polymer and oil.

* * * * *

UNITED STATES PATENT AND TRADEMARK OFFICE
CERTIFICATE OF CORRECTION

PATENT NO. : 5,155,148
DATED : October 13, 1992
INVENTOR(S) : Parker et al

It is certified that error appears in the above-identified patent and that said Letters Patent is hereby corrected as shown below:

At Column 5, line 6, delete "phenos" and insert therefor --phenols--.

At Column 5, line 8, delete "t-butylcatecho" and insert therefor --t-butylcatechol--.

At Column 6, line 11, delete "17 6" and insert therefor --17.6--.

At Column 10, line 7, delete "R" and insert therefor --$R^1$--.

At Column 10, line 8, delete "w is".

Signed and Sealed this

Fifteenth Day of February, 1994

Attest:

BRUCE LEHMAN

Attesting Officer

Commissioner of Patents and Trademarks